United States Patent [19]

Gupta et al.

[11] Patent Number: 4,655,770

[45] Date of Patent: Apr. 7, 1987

[54] SURFACE PASSIVATED INTRAOCULAR LENS

[75] Inventors: Amitava Gupta; Robert L. Van Osdel, both of Pasadena, Calif.

[73] Assignee: Ioptex, Inc., Azuza, Calif.

[21] Appl. No.: 741,758

[22] Filed: Jun. 6, 1985

[51] Int. Cl.$^4$ ................................................ A61F 2/14
[52] U.S. Cl. ........................................................ 623/1
[58] Field of Search ............................................ 623/1

[56] References Cited

U.S. PATENT DOCUMENTS 3,925,178  12/1975  Gesser et al. .................... 204/168
4,426,741   1/1984  Bittner ................................. 3/13

OTHER PUBLICATIONS

Antisoiling Technology: Theories of Surface Soiling and Performance of Antisoiling Surface Coatings by E. F. Cuddihy and P. B. Willis 11-15-84.

Materials in Intraocular Lenses by J. Reimer Wolter, M.D., p. 202, Apr. 25-28, 1985.

*Primary Examiner*—Gregory E. McNeill
*Attorney, Agent, or Firm*—Fulwider, Patton, Rieber, Lee & Utecht

[57] ABSTRACT

An intraocular lens is treated to form a modified passivated outer surface for reducing or eliminating biological reactions of inflammatory origin when the lens is implanted into an eye. The lens is formed from a conventional lens implant material, such as polymethyl methacrylate (PMMA), which is treated as required to create an outer surface region including a relatively high density of hydroxyl groups. This outer surface region is reacted with a selected fluorocarbon carried in a solution with a primer including bonding agents for bonding the fluorocarbon with respect to the hydroxyl groups, thereby creating a thin, substantially inert or passivated outer surface resistant to irritative reaction with tissue or cells when the lens is implanted into the eye.

45 Claims, No Drawings

SURFACE PASSIVATED INTRAOCULAR LENS

BACKGROUND THE INVENTION

This invention relates generally to improvements in polymer-based biological implant materials, such as intraocular lenses designed for implantation into the eye to replace a cataractous natural lens. More particularly, this invention relates to surface passivation of such implant materials or lenses to substantially reduce or eliminate adverse reactions with tissue or cells and further to substantially reduce or eliminate undesirable medical complications and/or patient discomfort.

Intraocular lenses and other biological implant devices formed at least in part from polymeric materials are relatively well known for use in a wide variety of medical implant applications. For example, plastic intraocular lenses are used extensively for implantation into the eye as a replacement for a natural lens which has been surgically removed typically due to opacification, referred to commonly as a cataract condition. Such intraocular lenses have traditionally been formed from polymethyl methacrylate (PMMA) selected for its optical properties and its historically perceived inertness to adverse tissue reaction when implanted into the eye. Other polymeric materials have also been used, such as polypropylene, to form support loops for intraocular lenses or forming other types of implant devices, wherein such materials have also been considered to be relatively inert.

Recent pathological studies have indicated, however, the consistent presence of at least some inflammatory reaction to a polymeric implant particularly with intraocular lenses implanted into the eye in contact or in close proximity with sensitive eye tissues or cells. More particularly, such studies have revealed the presence of a reactive membrane covering the intraocular lens wherein the membrane is formed from proteinaceous material and complex cellular structures commonly including macrophages associated with an irritative or inflammatory reaction. In many instances, these reactive membranes have remained relatively transparent from an optical standpoint and thus have not significantly reduced the clarity of patient vision. In other instances, however, the reactive membranes have transitioned to thicker, scar-like tissue, sometimes accompanied by fibrosis, with varying degrees of opacification resulting in undesirable vision loss.

There exists, therefore, a need for an improved biological implant material particularly for use as an intraocular lens, wherein the material is designed for substantially minimizing or eliminating inflammatory reaction with surrounding tissue or cells. The present invention fulfills this need and provides further related advantages.

SUMMARY OF THE INVENTION

In accordance with the invention, an improved polymeric biological implant is produced with a passivated outer surface by reacting said outer surface with a selected fluorocarbon, thereby creating a thin and highly inert outer surface layer. The surface passivation is especially applicable to intraocular lenses to prevent inflammatory reaction and resultant creation of reactive membranes when the intraocular lens is implanted into the eye.

In a preferred form of the invention, an intraocular lens is surface passivated, wherein the lens is formed from a conventional transparent polymeric material, typically polymethyl methacrylate (PMMA) with an appropriate geometry for the desired optical characteristics. This lens is surface treated as by ozone exposure followed by exposure to air to create outer surface region having a relatively high concentration of hydroxyl (OH) groups. Alternative lens or implant materials such as polypropylene or the like may include the requisite surface hydroxyl groups without requiring surface treatment.

The lens with the hydroxyl groups forming the outer surface region is then bathed in a fluorocarbon-based solution including a selected relatively inert fluorocarbon carried in solution with a primer selected for stable bonding of the fluorocarbon with respect to the hydroxyl groups. The lens is subsequently rinsed and dried leaving a thin substantially inert or passivated outer surface layer which is highly resistant to adverse reaction with living cells or tissue.

In the preferred form of the invention, the selected fluorocarbon-based solution comprises a perfluoro group $(CF_2)_x$ wherein X has a value within the range of about 6 to 12 and most preferably within the range of about 10 to about 12. The perfluoro group is placed in solution with the primer including at least two bonding agents for respective stable bonding to the perfluoro groups and to the hydroxyl groups on the lens outer surface region. More specifically, the preferred solution is prepared by dissolving an aminoethyl N-aminopropyl trimethoxysilane and perfluorodecanoic acid in a ratio of about 1:3 by weight in a carrier such as methanol to achieve a concentration of about $8 \times 10^{-6}$ to about $8 \times 10^3$, and preferably about $8 \times 10^{-5}$ moles/liter. This solution is processed to insure constituent reaction substantially to completion by refluxing at a temperature slightly below the boiling point of the carrier, such as about 50° C., for about 4 to about 16 hours, and preferably about 8-10 hours. The solution is then placed in a watertight container and should be used to treat the lens or other polymeric implant material within about 24 hours.

Other features and advantages of the present invention will become more apparent from the following detailed description.

DETAILED DESCRIPTION OF THE PREFERRED EMBODIMENT

The present invention relates to an improved polymer-based biological implant material particularly such as an intraocular lens designed for implantation into the eye. The outer surface of the material is treated and chemically modified to provide a passivated or substantially inert outer surface layer resistive to inflammatory or other adverse reaction with surrounding tissue or cells.

More particularly, intraocular lenses and many other types of biological implant devices have been constructed from polymer-based materials selected in part for their historically perceived inert properties when implanted into a living animal. For example, intraocular lenses for implantation into the eye subsequent to surgical removal of the natural crystalline lens, typically to correct a cataract condition, have traditionally been formed from polymethyl methacrylate (PMMA) chosen for its high transparency, low weight, and relatively high degree of tolerance by sensitive eye tissue and cells. Other implant materials, such as polypropylene used commonly to form support loops for intraocular lenses, are also selected in part for their relative nonreaction to living tissue and cells. See, for example, U.S. Pat. No. 4,426,741. However, particularly with intraocular lenses, recent pathological studies have indicated the presence of inflammatory or irritative reaction and have correlated such reactions with potential complications, such as uveitis and cystoid macular edema. Moreover, these inflammatory reactions have been indicated by the formation of reactive membranes and other cellular growths which, although not clincally significant in most cases, sometimes result in undesired opacification of the sight line through an intraocular lens. Similar inflammatory reactions with potential adverse effects are believed to occur with other types of biological implants and other polymer-based implant materials.

The present invention resides in a chemical surface modification of the outer surface of a biological implant, such as an intraocular lens, to enhance the physiological inertness thereof, without altering to any significant degree the remaining desired characteristics of the implant lens, such as transparency, lightness in weight, etc. The improved lens with modified outer surface layer is thus rendered biologically more stable to minimize or prevent inflammatory reaction within the eye. This surface modification takes place as a chemical molecular bonding directly with an outer surface region of the lens thereby avoiding the use of separately applied coatings and the like, which can biodegrade or release from the lens when exposed to body fluid over a prolonged period of time.

According to the invention, an intraocular lens is constructed in a conventional manner to include a lens body of a conventional transparent lens material, such as PMMA to have the desired size, shape, and optical properties. The PMMA lens is then treated to modify an outer surface region thereof to include a relatively high density of free hydroxyl (OH) groups available for molecular bonding subsequently to a fluorocarbon-based treatment solution, as will be described. In this regard, surface treatment of PMMA to form the hydroxyl bonding groups is required, whereas other types of polymeric materials, such as polypropylene used, for example, as support loops for a PMMA lens, inherently include a high proportion of hydroxyl bonding groups on the surface thereof without requiring initial surface treatment. Accordingly, with PMMA intraocular lenses, initial surface treatment to form the hydroxyl groups can be performed prior to installation of polypropylene loops onto the lens, if desired.

For PMMA intraocular lenses, a preferred initial surface treatment comprises exposing the lens to ozone gas to oxidize the lens outer surface followed by exposure of the lens to hydrogen as by exposure to air to hydrolyze the oxidized surface forming the desired hydroxyl groups. These steps may be conveniently carried out by placing one or more clean lenses on a metal plate within a bell jar supplied with ozone gas from a conventional ozone gas generator. More particularly, oxygen gas is flowed at a pressure of about 5 psig initially for about five minutes through a glass tube enclosing a pair of spaced electrodes. The oxygen gas flows further into the bell jar and is exhausted therefrom through a trap containing about 1.67 grams potassium iodide dissolved in about 100 milliliters (ml) water. An ozone generator dc power supply at about 13.5 Kv is then turned on with the oxygen flow continuing for roughly about fifteen minutes, achieving an ozone gas concentration within the bell jar atmosphere of about 500–700 parts/million. The power supply and the oxygen flow are then turned off in sequence and the bell jar raised to expose the lenses to a hydrated atmosphere, such as air, for several minutes. The lenses processed in this manner exhibit external surfaces defined by a high density of free hydroxyl groups.

The surface treated lenses with the outer region including the hydroxyl groups are next bathed in a treatment solution including a selected fluorocarbon and bonding agents for chemically bonding the fluoro carbon with respect to the hydroxyl groups, thereby providing an extremely thin, highly inert and chemically stable outer surface layer to the lenses. This treatment solution may also be applied advantageously to support loops for the lenses, wherein the support loops may be formed from polypropylene or other polymeric material.

In general, the preferred fluorocarbon-based treatment solution comprises a perfluorinated hydrocarbon carried in solution with two different molecular bonding agents selected for linking in a stable manner respectively between with the perfluorinated hydrocarbon and the hydroxyl groups on the lens. For example, the treatment solution broadly comprises a perfluoroalkane derivative, such as a perfluoroalkyl carboxylic acid in solution with an aminosilane, such as an alkoxyaminosilane. This preferred treatment solution thus includes alkoxy groups for attachment to the perfluoro groups and amine groups for bonding with the hydroxyl groups, and with the silane providing a linking structure for the alkoxy and amine groups. Alternately, the treatment solution may broadly comprise a silane carboxylic acid in solution with a perfluoro alkyl amine to provide generally the same bonding and linking groups to securely attach the highly inert perfluoro relative to the surface of the lens.

In accordance with one specific form of the invention, the fluorocarbon-based treatment solution is prepared by dissolving about 0.2 grams of an aminoethyl N-aminopropyl trimethoxysilane, such as that commercially available from Dow Corning Corp., Midland, Mich. under the designation Z-6020, in about 80 ml of an alcohol such as methanol (AR grade or better) with about 0.6 grams of perfluorodecanoic acid. This solution is placed in a round bottom flask and a standard reflux column is attached. The solution is refluxed to clarification at a temperature slightly below the boiling point of methanol, such as about 50° C., and for a period of several hours. A reflux period within the range of about 4–16 hours is preferred, and most preferably about 8–10 to insure progression of reaction of the solution constituents substantially to completion. The reaction time period can be decreased, if desired, by increasing the temperature, and standard titration techniques can be used to determine the completion of constituent reaction. The resultant treatment solution is then placed in an appropriate beaker, diluted with about 320 ml of additional methanol, and stored in a watertight manner until use. This solution will remain stable for use in surface-treating lenses for about 24 hours and constitutes a sufficient quantity of solution to treat about 100,000 intraocular lenses.

The thus-prepared treatment solution includes perfluoro groups $(CF_2)_x$ wherein $(x)$ is 10. Moreover, the perfluoro solution concentration is about $8 \times 10^{-5}$ moles per liter. This treatment solution has been found, when bonded with the hydroxyl groups on the lens surface, to provide a substantially complete yet environmentally stable surface coverage of the lens surface by the perfluoro thereby yielding a highly inert modified surface layer of significantly reduced toxicity in comparison with PMMA and of extremely thin depth on the order of about 10 Angstroms to about 1 micron. To insure adequate surface coverage with perfluoro and further to insure formation of surface compounds which will remain stable when the lens is implanted into the eye, it is preferred that (x) be within the range of about 6 to 12. It is further believed that the solution concentration should be within the range of about $8 \times 10^{-6}$ to about $8 \times 10^{-3}$ moles/liter.

The treatment solution is applied to one or more of the intraocular lenses by dipping or bathing the lenses in the treatment solution with lenses preferably separated physically from one another. Alternately, the lenses may be placed into an open receptacle and the treatment solution poured over the lenses, with the lenses again being maintained in physical separation to insure complete wetting of the entire outer surface of each lens. In either technique, the lenses are maintained completely immersed in the treatment solution for about 5 minutes to about 10 minutes. The lenses are then removed from the treatment solution, or vice versa, and the lenses are allowed to dry in air, requiring about 4-5 minutes, to insure surface reaction to completion. Methanol (AR grade or better) or other appropriate alcohol is then used to rinse unreacted material from the lenses, after which the lenses may be appropriately sterilized and packaged as required, ready for surgical implantation into the eye of a patient.

Each lens treated in accordance with the above-described procedure has its outer surface chemically modified to include a substantially complete outer surface layer with the inert perfluoro groups. This outer surface layer is visually undetectable and therefore does not alter the otherwise highly desirable transparency and other optical characteristics of the lens. The toxicity of the lens outer surface to surrounding tissue or cells, however, is substantially reduced to correspondingly reduce inflammatory or irritative reactions and the various potential complications associated therewith. Alternately stated, the outer surface layer of the lens is chemically passivated for improved clinical performance and patient comfort without any adverse effect upon optical performance.

A variety of modifications and improvements to the improved implant material and treatment method described herein are believed to be apparent to those skilled in the art. Accordingly, no limitation on the invention is intended by way of the description therein, except as set forth in the appended claims.

What is claimed is:

1. An intraocular lens comprising a lens formed from polymethyl methacrylate and having an outer surface layer defined by a relatively inert fluorocarbon chemically bonded with respect to the lens 2. The intraocular lens of claim 1 wherein said fluorocarbon comprises a perfluorinated hydrocarbon.

3. The intraocular lens of claim 1 wherein said fluorocarbon comprises a perfluoro $(CF_2)_x$ wherein (x) is from about 6 to about 12.

4. The intraocular lens of claim 3 wherein (x) is 10.

5. The intraocular lens of claim 1 wherein said lens includes means formed from a polymeric material for supporting said lens within the eye.

6. The intraocular lens of claim 5 wherein said support means is formed from polypropylene.

7. The intraocular lens of claim 5 wherein said support means also includes an outer surface layer defined by said relatively inert fluorocarbon bonded thereto.

8. An intraocular lens comprising a lens body formed from a polymeric material, said lens body including a substantially uninterrupted outer surface layer defined by a relatively inert fluorocarbon.

9. The intraocular lens of claim 8 further including means formed from a polymeric material for supporting said lens body within the eye, said outer surface layer also covering said support means.

10. The intraocular lens of claim 9 wherein said polymeric material forming said lens body comprises polymethyl methacrylate.

11. The intraocular lens of claim 9 wherein said polymeric material forming said lens body comprises polymethyl methacrylate having a substantially oxidized outer surface region.

12. The intraocular lens of claim 11 wherein said outer surface region includes a relatively high concentration of hydroxyl groups.

13. The intraocular lens of claim 9 wherein said polymeric material forming said support means is polypropylene.

14. The intraocular lens of claim 8 wherein said fluorocarbon comprises a perfluorinated hydrocarbon $(CF_2)_x$ wherein (x) is from about 6 to about 12.

15. The intraocular lens of claim 8 wherein said outer surface layer is chemically bonded to said lens body.

16. A biological implant comprising an implant device formed from a polymeric material, and an outer surface layer chemically bonded to said implant device to substantially cover the entire outer surface area thereof to be exposed to tissue when implanted, said outer surface layer including a relatively inert fluorocarbon.

17. The implant of claim 16 wherein said fluorocarbon comprises a perfluorinated hydrocarbon.

18. The implant of claim 16 wherein said fluorocarbon comprises a perfluoro $(CF_2)_x$ wherein (x) is from about 6 to about 12.

19. The implant of claim 18 wherein (x) is 10.

20. The implant of claim 16 wherein said polymeric material has a substantially oxidized outer surface.

21. The implant of claim 20 wherein said polymeric material comprises polymethyl methacrylate having its outer surface substantially oxidized.

22. The implant of claim 22 wherein said implant device comprises an intraocular lens.

23. A method of producing an intraocular lens comprising the steps of:

forming a transparent lens body from a polymeric material selected to have a predetermined set of optical properties; and forming an outer surface layer substantially completely covering the lens body, the outer surface layer including a relatively inert fluorocarbon to substantially reduce the toxicity of the lens when implanted into the eye.

24. The method of claim 23 wherein said lens body forming step includes the step of substantially oxidizing the outer surface of said lens body, and wherein said outer surface layer forming step comprises chemically bonding the fluorocarbon to the outer surface of said lens body.

25. The method of claim 24 wherein the lens body is formed from polymethyl methacrylate, and wherein said oxidizing step comprises exposing the lens body to an ozone atmosphere for a period of time and at a concentration sufficient to substantially oxidize the lens body outer surface, and then exposing the lens body to a hydrated atmosphere to form a relatively high concentration of hydroxyl groups at the lens body outer surface.

26. The method of claim 25 wherein the hydrated atmosphere is air.

27. The method of claim 23 wherein the fluorocarbon comprises a perfluorinated hydrocarbon.

28. The method of claim 23 wherein the fluorocarbon comprises a perfluoro $(CF_2)_x$ wherein (x) is from about 6 to about 12.

29. The method of claim 28 wherein (x) is 10.

30. The method of claim 23 further including the steps of forming support means on the lens body for supporting the lens body when implanted into the eye, and forming said outer surface layer to substantially completely cover the support means.

31. An intraocular lens formed by the process of claim 23.

32. A method of producing an intraocular lens for implantation into the eye, comprising the steps of:
  forming a generally transparent lens body from a polymeric material selected to have a predetermined set of optical properties and to have a substantially oxidized outer surface over substantially the entire outer surface area thereof;
  preparing a treatment solution including relatively inert fluorocarbon bonding groups carried in solution with a primer including bonding agents for chemically bonding the fluorocarbon bonding groups with respect to the oxidized outer surface of the lens body; and
  covering the lens body with the treatment solution for a period of time sufficient to permit bonding of said fluorocarbon bonding groups with respect to the lens body.

33. The method of claim 32 wherein the polymeric material comprises polymethyl methacrylate, and wherein said lens body forming step comprises substantially oxidizing the outer surface thereof in an ozone atmosphere and then exposing the outer surface to a hydrated atmosphere to form a relatively high concentration of hydroxyl groups at the lens body outer surface.

34. The method of claim 32 wherein the treatment solution includes perfluoro $(CF_2)_x$ bonding groups wherein (x) is from about 6 to about 12, and wherein said primer bonding agents molecularly bond said perfluoro bonding groups onto the outer surface of the lens body to form a relatively inert outer surface layer having a thickness within the range of from about 10 Angstroms to about 1 micron.

35. The method of claim 34 wherein (x) is 10.

36. The method of claim 34 wherein the solution concentration of the perfluoro bonding groups is from about $8 \times 10^{-6}$ to about $8 \times 10^{-3}$ moles/liter.

37. The method of claim 36 wherein the solution concentration is about $8 \times 10^{-5}$ moles/liter.

38. The method of claim 34 wherein said treatment solution preparing step comprises dissolving a perfluoro alkane derivative in alcohol with an aminosilane.

39. The method of claim 34 wherein said treatment solution preparing step comprises dissolving a perfluoro alkyl amine in alcohol with silane carboxylic acid.

40. The method of claim 34 wherein said treatment solution preparing step comprises dissolving an aminoethyl N-aminopropyl trimethoxysilane and perfluorodecanoic acid in a ratio of about 1:3 by weight in alcohol, and refluxing the resultant solution for about 4 to about 16 hours.

41. The method of claim 40 wherein said refluxing step is continued at a temperature slightly below the boiling point of the alcohol for about 8-10 hours.

42. The method of claim 40 wherein the refluxed solution is diluted in additional alcohol to achieve a perfluoro concentration of about $8 \times 10^{-5}$ moles/liter.

43. The method of claim 40 further including the step of removing the lens body from the treatment solution and rinsing unreacted material therefrom.

44. An intraocular lens formed by the process of claim 43.

45. A method of producing a biological implant, comprising the steps of:
  forming an implant device from a selected polymeric material having a desired set of physical properties; and
  forming an outer surface layer substantially completely covering the implant device, the outer surface layer including a relatively inert fluorocarbon to substantially reduce toxicity of the device when implanted.

* * * * *